United States Patent [19]
Dayton et al.

[11] Patent Number: 5,932,793
[45] Date of Patent: Aug. 3, 1999

[54] APPARATUS AND METHOD FOR DETERMINING THERMOPHYSICAL PROPERTIES USING AN ISOCHORIC APPROACH

[75] Inventors: Troy Dayton; Steve Beyerlein, both of Moscow, Id.; Jeffrey L. Savidge, Algonquin, Ill.; Anthony R. H. Goodwin, Moscow, Id.

[73] Assignee: Gas Research Institute, Chicago, Ill.

[21] Appl. No.: 08/903,069

[22] Filed: Jul. 30, 1997

Related U.S. Application Data

[60] Provisional application No. 60/022,941, Aug. 1, 1996.
[51] Int. Cl.$^6$ ............................ G01N 9/00; G01N 29/02; G01F 15/04
[52] U.S. Cl. ........................................ 73/24.05; 73/23.28
[58] Field of Search ................................ 73/24.05, 23.28, 73/23.2, 1 G, 861.27; 364/509, 571.03

[56] References Cited

U.S. PATENT DOCUMENTS

| | | | |
|---|---|---|---|
| 4,262,523 | 4/1981 | Stansfeld | 73/30 |
| 4,489,592 | 12/1984 | Pacanowski et al. | 73/30 |
| 4,663,977 | 5/1987 | Vander Heyden | 73/861.27 |
| 4,872,335 | 10/1989 | Tsuruoka et al. | 73/30 |
| 5,159,843 | 11/1992 | Shakkottai et al. | 73/24.05 |
| 5,285,675 | 2/1994 | Colgate et al. | 73/23.2 |
| 5,311,447 | 5/1994 | Bonne | 364/509 |
| 5,343,758 | 9/1994 | Ingrain et al. | 73/861.02 |
| 5,693,873 | 12/1997 | Thuries et al. | 73/23.28 |

OTHER PUBLICATIONS

Thermodynamic Properties of Gaseous Argon at Temperatures Between 110 and 450 K and Densities up to 6.8 Mol·dm$^{-3}$ Determined from the Speed of Sound, by A. F. Estrada–Alexanders and J.P.M. Trusler, International Journal of Thermophysics, vol. 17, No. 6, 1996, Apr. 1996.

The Speed of Sound and Derived Thermodynamic Properties of Ethane at Temperature between 220 K and 450 K and Pressures up to 10.5 MPa, by A.F. Estrada–Alexanders and J. P. M. Trusler, Department of Chemical Engineering and Chemical Technology, Imperial College, London SW7 2BY, United Kingdom, J. Chem. Thermodynamics 1997, pp. 29, 991–1015. Jun. 1997.

Fluid Properties from the Speed and Absorption of Sound, The Adam Hilger Series on Measurement Science and Technology: Physical Acoustics and Metrology of Fluids by J. P. M. Trusler, Department of Chemical Engineering, Imperial College, London, Adam Hilger, Bristol, Philadelphia and New York, 1991, pp. 1–9. Jan. 1991.

The Speed of Sound and Dervied Thermodynamic Properties of Methane at Temperatures between 275 K and 375 K and pressures up to 10 MPa by J. P. M. Trusler and M. Zarari, Department of Chemical Engineering and Chemical Technology, Imperial College, London SW7 2BY, United Kingdom, J. Chem. Thermodynamics 1992, pp. 24, 973–991. Feb. 1992.

Determination of Thermodynamic Properties from the Speed of Sound by A. F. Estrada–Alexanders, J. P. M. Trusler, and M. P. Zarari, International Journal of Thermophysics, vol. 16, No. 3, 1995, pp. 663–673. Mar. 1995.

*Primary Examiner*—Hezron Williams
*Assistant Examiner*—J. David Wiggins
*Attorney, Agent, or Firm*—Pauley Petersen Kinne & Fejer

[57] ABSTRACT

The instant invention relates to a method and apparatus to determine the thermodynamic properties of a gas medium without making a determination of gas composition. In the instant invention, the pressure and speed of sound of a gas medium in a vessel are determined at multiple temperature points. According to the preferred embodiment, this information may be on a single isochore. Once the physical information is determined, an interpolation routine is executed by which initial estimated parameters such as the density and the compressibility of the gas medium will converge to accurate values. From these parameters, the thermophysical properties of the gas medium may be determined.

25 Claims, 8 Drawing Sheets

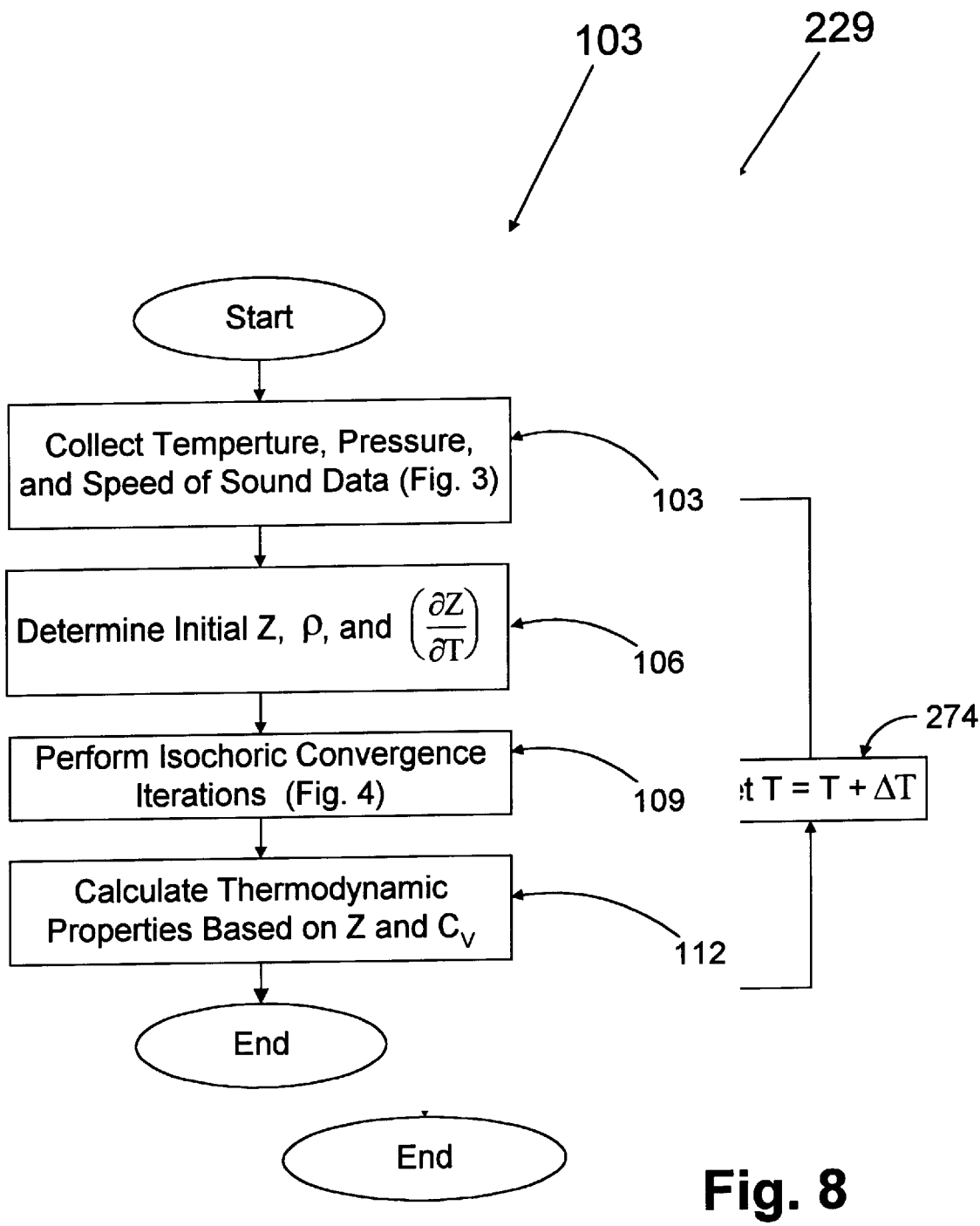

APPARATUS AND METHOD FOR DETERMINING THERMOPHYSICAL PROPERTIES USING AN ISOCHORIC APPROACH

This application claims priority to co-pending and commonly assigned U.S. provisional patent application entitled, "Obtaining Thermophysical Properties of Natural Gas Mixtures from Speed of Sound Data", filed Aug. 1, 1996 and accorded Ser. No. 60/022,941. The foregoing document is incorporated herein by reference in its entirety. The subject matter of this document is also related to the U.S. patent application entitled "Apparatus and Method for Determining Thermophysical Properties Using an Isobaric Approach", filed concurrently herewith and accorded Ser. No. 08/903,314.

FIELD OF THE INVENTION

This invention relates to the field of measuring physical properties of gasses, and more particularly, of measuring the physical properties of natural gasses.

BACKGROUND OF THE INVENTION

Accurate thermophysical properties of hydrocarbons are essential for analyzing processes related to liquification, transportation, processing and storage of gaseous fuels. Among the properties of interest are the compression factor, heat capacity, entropy, enthalpy and others. These properties must be known about various fluids or gasses which are made of a mixture of gasses. Such parameters are used in determining the precise makeup of storage vessels and processing equipment as well as a multitude of other applications.

These properties are generally calculated from an equation of state using so called look up tables for the particular gas. However, these lookup tables do not include parameters for gasses that are composed of a mixture of elements. Such mixtures are referred to as multi-component gasses or fluids. Also, the accuracy of properties calculated from an equation of state depends upon the accuracy of the experimental data used in the fitting process.

The state-of-the-art technology used to measure the above characteristics include equipment to ascertain the precise chemical makeup of a multi-component gas. Generally such equipment and methods are expensive to use.

For the reasons identified in the foregoing discussion, there is a need for a low cost system to determine the thermophysical properties of a multi-component gas or fluid.

SUMMARY OF THE INVENTION

The instant invention involves first and second embodiments of a method and apparatus for the accurate determination of the thermophysical properties of a multi-component gas. The apparatus of the first embodiment involves the measuring of temperature, speed of sound-, and pressure data of a medium in a vessel at a constant density. The vessel is fitted with the appropriate components to obtain these parameters. These components interface with a computing system.

In the method according to the first embodiment, the temperature of the medium in the vessel is varied over a specified range, wherein measurements of the speed of sound and pressure are recorded. Next a convergence process is implemented on the data collected in which the heat capacity and compressibility of the medium are accurately determined. Finally, from these parameters, other thermophysical properties of comparable accuracy may be determined.

The apparatus of the second embodiment involves the measuring of temperature and speed of sound data of a medium in a vessel at constant pressure. The vessel is fitted with the appropriate components to obtain these parameters. These components also interface with a computing system.

In the method according to the second embodiment, the temperature of the medium in the vessel is varied over a specified range, wherein measurements of the speed of sound are recorded at constant pressure. Next a convergence process is implemented on the data collected in which the heat capacity and compressibility of the medium are accurately determined. Finally, from these parameters, other thermophysical properties of comparable accuracy may be determined.

Other features and advantages of the present invention will become apparent to one with skill in the art upon examination of the following drawings and detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily shown to scale, emphasis instead being placed upon clearly illustrating the principles of the present invention. In the drawings, like reference numerals designate corresponding parts throughout the several views.

FIG. 8 is a flow diagram illustrating the method of accomplishing the isobaric convergence step of FIG. 6.

DETAILED DESCRIPTION OF THE PREFERRED EMBODIMENT

Figure 1:
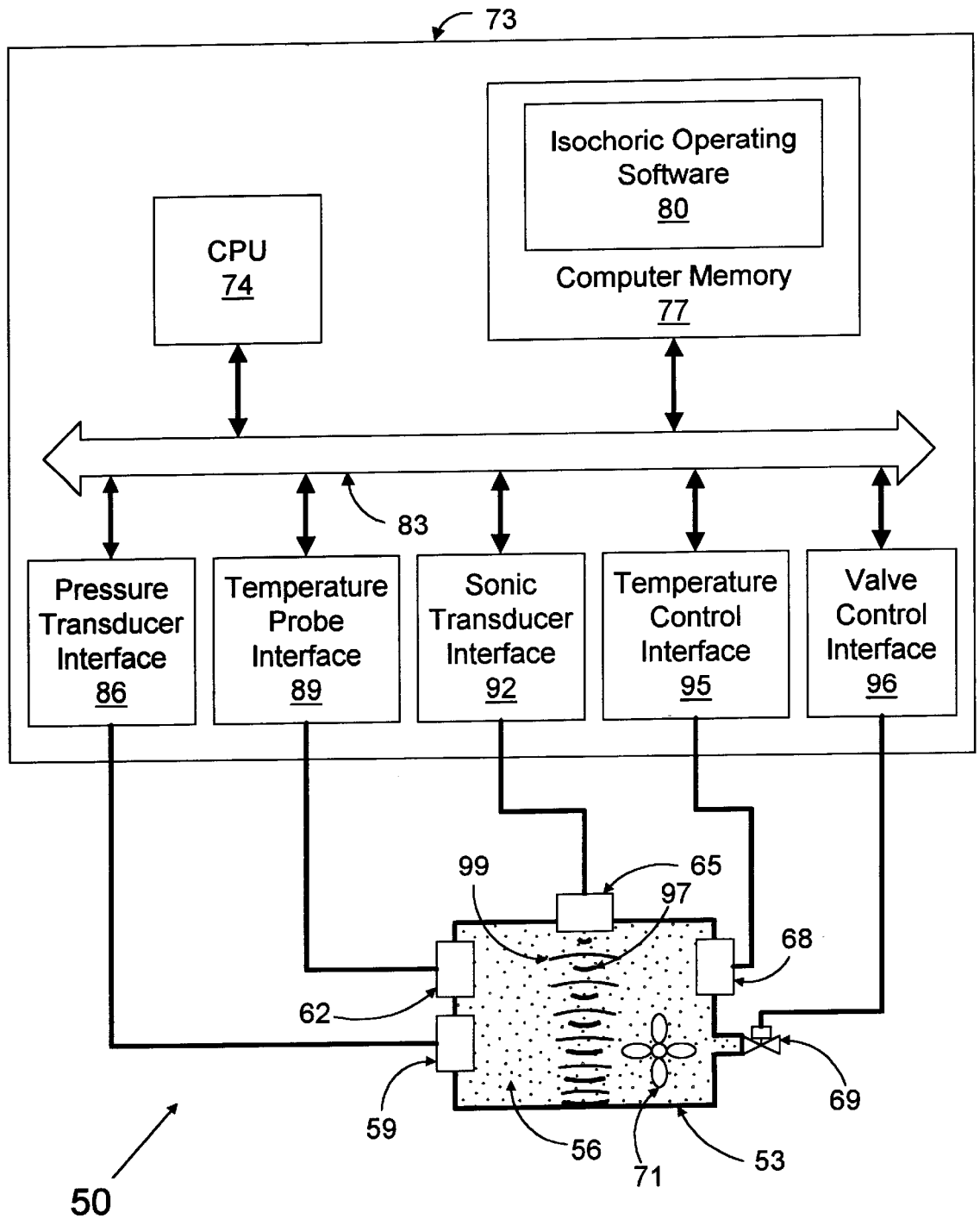
FIG. 1 is a drawing illustrating an system used in performing the method according to the first embodiment of the instant invention.

The present invention involves the derivation of the isobaric and isochoric equations for transforming speed of sound data into compression factor and heat capacity values from which other thermophysical properties may be determined. The following discussion shows this derivation. The development begins with the definition of the thermophysical speed of sound in an unbound fluid, $$u^2 = \left(\frac{\partial P}{\partial \rho}\right)_S \qquad 1.0$$

where P is pressure, $\rho$ is molar density, and S is entropy. The cyclical relation $$\left(\frac{\partial P}{\partial \rho}\right)_S \left(\frac{\partial \rho}{\partial S}\right)_P \left(\frac{\partial S}{\partial P}\right)_\rho = -1 \qquad 1.1$$

can be substituted into equation 1.0 to give $$u^2 = \left(\frac{\partial S}{\partial \rho}\right)_P \left(\frac{\partial P}{\partial S}\right)_\rho \qquad 1.2$$

Using thermophysical relations, equation 1.2 can be transformed into two different sets of differential equations as will be shown.

Derivation of Isochoric Speed of Sound Equations

In the first embodiment, the speed of sound data is measured in an isochoric measurement scheme. If entropy is assumed to be a function of temperature and density, the total derivative of entropy can be written as $$dS = \left(\frac{\partial S}{\partial T}\right)_\rho dT + \left(\frac{\partial S}{\partial \rho}\right)_T d\rho. \qquad 2.0$$

The partial derivatives in equation 2.0 can be defined using the definition of the isochoric heat capacity $$\left(\frac{\partial S}{\partial T}\right)_\rho = \frac{C_V}{T}, \qquad 2.1$$

and the Maxwell relation $$\left(\frac{\partial S}{\partial \rho}\right)_T = -\frac{1}{\rho^2}\left(\frac{\partial P}{\partial T}\right)_\rho \qquad 2.2$$

Equations 2.1 and 2.2 are substituted for the partial differentials in equation 2.0, the resulting equation being $$dS = \frac{C_V}{T} dT - \frac{1}{\rho^2}\left(\frac{\partial P}{\partial T}\right) d\rho. \qquad 2.3$$

Next, equation 2.3 is divided by the partial differential of density at constant pressure. The resulting equation $$\left(\frac{\partial S}{\partial \rho}\right)_P = \frac{C_V}{T}\left(\frac{\partial T}{\partial \rho}\right)_P - \frac{1}{\rho^2}\left(\frac{\partial P}{\partial T}\right)_\rho \qquad 2.4$$

is then substituted into equation 1.2. Also, equation 2.3 is divided by the partial of pressure at constant density. The second resulting equation $$\left(\frac{\partial S}{\partial P}\right)_\rho = \frac{C_V}{T}\left(\frac{\partial T}{\partial P}\right)_\rho \qquad 2.5$$

is also substituted into equation 1.2. With these substitutions, equation 1.2 becomes $$u^2 = -\left[\frac{C_V}{T}\left(\frac{\partial T}{\partial \rho}\right)_P - \frac{1}{\rho^2}\left(\frac{\partial P}{\partial T}\right)_\rho\right]\frac{T}{C_V}\left(\frac{\partial P}{\partial T}\right)_\rho, \qquad 2.6$$

which is further simplified into $$u^2 = \left(\frac{\partial P}{\partial \rho}\right)_T + \frac{T}{\rho^2 C_V}\left(\frac{\partial P}{\partial T}\right)_\rho^2. \qquad 2.7$$

Next the partial derivative of equation 2.1 of the isochoric heat capacity with respect to molar density at constant temperature reveals $$\left(\frac{\partial C_V}{\partial \rho}\right)_T = T\frac{\partial}{\partial \rho}\left[\left(\frac{\partial S}{\partial T}\right)_\rho\right]_T. \qquad 2.8$$

Using the Maxwell relation given in equation 2.2, equation 2.8 can be expressed as $$\left(\frac{\partial C_V}{\partial \rho}\right)_T = -\frac{T}{\rho^2}\left(\frac{\partial^2 P}{\partial T^2}\right)_\rho. \qquad 2.9$$

Although equations 2.7 and 2.9 can be solved for molar density and isochoric heat capacity, it is preferable to solve these equations with the more slowly varying compression factor, Z, instead of the molar density. Thus equation 2.7 becomes $$u^2 = \frac{RT}{M}\left\{\left[Z + \rho\left(\frac{\partial Z}{\partial \rho}\right)_T\right] + \frac{R}{C_V}\left[Z + T\left(\frac{\partial Z}{\partial T}\right)_\rho\right]^2\right\}, \qquad 2.10$$

and equation 2.9 becomes $$\left(\frac{\partial C_V}{\partial \rho}\right)_T = -\frac{R}{\rho}\left[2T\left(\frac{\partial Z}{\partial T}\right)_\rho + T^2\left(\frac{\partial^2 Z}{\partial T^2}\right)_\rho\right], \qquad 2.11$$

where M is the molecular mass and R is the universal gas constant. Equations 2.10 and 2.11 can be rearranged to solve for $C_V$ and $$\left(\frac{\partial^2 Z}{\partial T^2}\right)_\rho,$$

resulting in $$C_V = \frac{R\left[Z + T\left(\frac{\partial Z}{\partial T}\right)_\rho\right]^2}{u^2\left(\frac{M}{RT}\right) - Z - \rho\left(\frac{\partial Z}{\partial \rho}\right)_T} \qquad 2.12$$

$$\left(\frac{\partial^2 Z}{\partial T^2}\right)_\rho = -\frac{\frac{\rho}{R}\left(\frac{\partial C_V}{\partial \rho}\right)_T + 2T\left(\frac{\partial Z}{\partial T}\right)_\rho}{T^2}. \qquad 2.13$$

The solution of these two equations requires initial values of Z and $$\left(\frac{\partial Z}{\partial T}\right)_\rho$$

on all isochores at the lowest temperature. Finally, the compression factor is solved for using the above derived variables using the following Taylor Series Approximations:

$$Z_1 = Z_0 + \Delta T\left(\frac{\partial Z_0}{\partial T}\right)_\rho + \frac{1}{2}\Delta T^2\left(\frac{\partial^2 Z_0}{\partial T^2}\right)_\rho, \text{ and} \quad 2.14$$

$$\left(\frac{\partial Z_1}{\partial T}\right)_\rho = \left(\frac{\partial Z_0}{\partial T}\right)_\rho + \Delta T\left(\frac{\partial^2 Z^0}{\partial T^2}\right)_\rho. \quad 2.15$$

Derivation of Isobaric Speed of Sound Equations

In a second embodiment of the invention, speed of sound data is measured in an isobaric scheme. If entropy is assumed to be a function of temperature and pressure, the total derivative of entropy can be written as $$dS = -\left(\frac{\partial S}{\partial T}\right)_P dT + \left(\frac{\partial S}{\partial P}\right)_T dP. \quad 3.0$$

The partial derivatives in equation 3.0 are defined using the definition of the isobaric heat capacity $$C_P = T\left(\frac{\partial S}{\partial T}\right)_P, \quad 3.1$$

and the Maxwell relation $$\left(\frac{\partial S}{\partial P}\right)_T = -\frac{1}{\rho^2}\left(\frac{\partial \rho}{\partial T}\right)_P. \quad 3.2$$

Equation 3.0 can then be rewritten as $$dS = \frac{C_P}{T}dT + \frac{1}{\rho^2}\left(\frac{\partial \rho}{\partial T}\right)_P dP. \quad 3.3$$

Equation 3.3 is then divided by the partial derivative of density at constant pressure. The resulting equation $$\left(\frac{\partial S}{\partial \rho}\right)_P = \frac{C_P}{T}\left(\frac{\partial T}{\partial \rho}\right)_P. \quad 3.4$$

is substituted into equation 1.2. Also, equation 3.3 is divided by the partial derivative of pressure at constant density. The resulting equation $$\left(\frac{\partial S}{\partial P}\right)_\rho = \frac{C_P}{T}\left(\frac{\partial T}{\partial P}\right)_\rho - \frac{1}{\rho^2}\left(\frac{\partial \rho}{\partial T}\right)_P. \quad 3.5$$

is also substituted into equation 1.2. With these substitutions, equation 1.2 becomes $$u^2 = -\frac{C_P}{T}\left(\frac{\partial T}{\partial \rho}\right)_P\left[\frac{C_P}{T}\left(\frac{\partial T}{\partial P}\right)_\rho + \frac{1}{\rho^2}\left(\frac{\partial \rho}{\partial T}\right)_P\right]^{-1} \quad 3.6$$

which can be simplified into $$u^2 = \left[\left(\frac{\partial \rho}{\partial P}\right)_T + \frac{T}{\rho^2 C_P}\left(\frac{\partial \rho}{\partial T}\right)_P^2\right]^{-1}. \quad 3.7$$

Next, the partial derivative of the isobaric heat capacity of equation 3.7 with respect to pressure at constant temperature is taken, resulting in $$\left(\frac{\partial C_P}{\partial P}\right)_T = T\left(\frac{\partial}{\partial P}\right)\left[\left(\frac{\partial S}{\partial T}\right)_P\right]_T. \quad 3.8$$

Using the Maxwell relation given in equation 3.2, equation 3.8 becomes $$\left(\frac{\partial C_P}{\partial P}\right)_T = -T\left(\frac{\partial^2 \rho^{-1}}{\partial T^2}\right)_P \quad 3.9$$

Although equations 3.7 and 3.9 can be solved for molar density and isobaric heat capacity, it is preferable to solve these equations with the more slowly varying compression factor, Z, instead of the molar density. Thus equation 2.7 becomes $$u^2 = \frac{M}{RTZ^2}\left[Z - P\left(\frac{\partial Z}{\partial P}\right)_T\right] - \left(\frac{1}{C_P TZ^2}\right)\left[Z + T\left(\frac{\partial Z}{\partial T}\right)_P\right]^2 \quad 3.10$$

and equation 2.9 becomes $$\left(\frac{\partial C_P}{\partial P}\right)_T = -\frac{R}{P}\left[2T\left(\frac{\partial Z}{\partial T}\right)_P + T^2\left(\frac{\partial^2 Z}{\partial T^2}\right)_P\right]. \quad 3.11$$

where M is the molecular mass, and R is the universal gas constant. Equations 3.10 and 3.11 are then rearranged to solve for $C_P$ and $$\left(\frac{\partial^2 Z}{\partial T^2}\right)_P,$$

resulting in $$C_P = \frac{R\left[Z + T\left(\frac{\partial Z}{\partial T}\right)_P\right]^2}{u^{-2}\left(\frac{RTZ^2}{M}\right) - Z + P\left(\frac{\partial Z}{\partial P}\right)_T}, \text{ and} \quad 3.12$$

$$\left(\frac{\partial^2 Z}{\partial T^2}\right)_P = -\frac{\frac{P}{R}\left(\frac{\partial C_P}{\partial P}\right)_T + 2T\left(\frac{\partial Z}{\partial T}\right)_P}{T^2}. \quad 3.13$$

The solution of equations 3.12 and 3.13 require initial values for Z and $$\left(\frac{\partial Z}{\partial T}\right)_P$$

on all isobars at the lowest temperature. Finally, the compression factor is solved for using the above derived variables using the following Taylor Series Approximations:

$$Z = Z_0 + \Delta T \left(\frac{\partial Z_0}{\partial T}\right)_P + \frac{1}{2}\Delta T^2 \left(\frac{\partial^2 Z_0}{\partial T^2}\right)_P, \text{ and} \quad 3.14$$

$$\left(\frac{\partial Z}{\partial T}\right)_P = \left(\frac{\partial Z_0}{\partial T}\right)_P + \Delta T \left(\frac{\partial^2 Z_0}{\partial T^2}\right)_P. \quad 3.15$$

Convergence Using Isochoric Equations

In the following discussion, the first embodiment of the present invention is described in which the formulas derived above relating to the isochoric speed of sound are employed to ascertain accurate thermophysical properties of a volume of a particular multi-component medium.

To begin, a temperature range is specified over which measurements of the speed of sound and the pressure of the particular volume of multi-component medium will be taken. Also, a temperature step $\Delta T$ is chosen at which to take these measurement across the range specified. Note, however, that the temperature step $\Delta T$ need not be uniform across the temperature range. Uniformity may be achieved by interpolation techniques as known to those skilled in the art.

Next, the temperature of the medium is brought to either the low end, $T_{LOW}$, or the high end, $T_{HIGH}$, of the temperature range to begin taking measurements of physical parameters. The deciding factor as to whether to us $T_{LOW}$ or $T_{HIGH}$ as the beginning point is that no particular component of the medium be at or near the liquid stage. If no component is at or near the liquid stage at $T_{LOW}$, then this temperature may be used as the starting point. This is to ensure that the multi-component medium is a uniform mixture.

In the case where $T_{LOW}$ is chosen as to start, the temperature of the medium is then raised in steps by $\Delta T$. In the case where $T_{HIGH}$ is chosen as to start, the temperature of the medium is lowered in steps by $\Delta T$. In either case, at each step the pressure P and speed of sound u of the medium are measured. This cycle of raising or lowering the temperature in steps of $\Delta T$ and measuring the pressure and speed of sound at each step is continued until measurements have been taken across the entire specified temperature range. In the first embodiment, the temperatures, pressures and speed of sound for each temperature increment are stored in memory for further evaluation. During the entire process, the density $\rho$ is kept nearly constant. There may be slight fluctuation of the density $\rho$ due to deformity of any vessel in which the medium is held caused by changing pressure P. However, the substance of the medium will remain the same.

After the values of the temperature, pressure, and speed of sound have been determined for each interval across the specified range, an iterative process based on these measurements is undertaken in which the thermophysical properties of the multi-component medium are ascertained. According to the first embodiment, new and more accurate values for the compressibility Z, density $\rho$ and $$\left(\frac{\partial Z}{\partial T}\right)$$

are calculated for each $\Delta T$ starting at $T_{LOW}$ using the Z, $\rho$ and $$\left(\frac{\partial Z}{\partial T}\right)$$

from the previous calculation as initial values, thereby converging on more precise values for these properties across the specified temperature range. For the first calculation at the first $\Delta T$, an estimate of the Z, $\rho$ and $$\left(\frac{\partial Z}{\partial T}\right)$$

are used as initial values.

A single iteration of the process comprises performing the calculations for all $\Delta T$'s across the specified temperature range. The density $\rho$ that results from each iteration is used as the initial density p in the subsequent iteration. Based on the new density that emerges, the initial estimates of Z and $$\left(\frac{\partial Z}{\partial T}\right)$$

are updated. With each iteration performed, the density will converge to the actual value of the density of the multi-component medium. Likewise, the specific heat $C_V$ and compressibility Z calculated in each iteration will converge to accurate values as well. In the preferred form of the first embodiment, the iterations are performed on a computing system which will allow many iterations to be performed in a small period of time.

To describe in detail the calculations performed for each $\Delta T$, first, initial values for the compressibility Z, density $\rho$, and $$\left(\frac{\partial Z}{\partial T}\right)$$

of the medium are determined. These values may be estimated in one of several ways, including the use of any equation of state or other methods known to those skilled in the art. In particular, detailed knowledge of the gas composition is not required to obtain the values needed to initiate the calculations. A reasonable estimate of the gas composition from which the initial compressibility Z, density $\rho$, and $$\left(\frac{\partial Z}{\partial T}\right)$$

can be determined using an equation of state is recommended. In the first embodiment, the equation of state disclosed in the American Gas Association Report No. 8, version 1.2 dated July, 1994 is used due to its relatively greater accuracy as known by those skilled in the art. A reasonable estimate for the compositions of typical natural gasses could be, for example, pure methane or any of the appropriate natural gas compositions in American Gas Association Report No. 8. Also, these estimates can be made on the basis of other measurements as known to those skilled in the art or based on experience with the particular type of fluid, the compositions of which are generally known over a period of time.

Once values for each of these variables are estimated, the numerical derivative of the compressibility Z with respect to density p at constant temperature, denoted as $$\left(\frac{\partial Z}{\partial \rho}\right)_T,$$

is determined. The numerical derivative may be expressed as $$\left(\frac{\partial Z}{\partial \rho}\right)_T = \frac{Z(\rho + \Delta\rho, T) - Z(\rho - \Delta\rho, T)}{2\Delta\rho}.$$

Generally, the numerical derivative $$\left(\frac{\partial Z}{\partial \rho}\right)_T$$

may be calculated from measurements at an isochore both above and below the current isochore as known to those skilled in the art.

Next, the isochoric heat capacity $C_V$ is found using previously derived equation 2.12 which, once again, is expressed as $$C_V = \frac{R\left[Z + T\left(\frac{\partial Z}{\partial T}\right)_\rho\right]^2}{u^2\left(\frac{M}{RT}\right) - Z - \rho\left(\frac{\partial Z}{\partial \rho}\right)_T}. \quad 2.12$$

where M is the molecular mass and R is the universal gas constant.

Once the isochoric heat capacity $C_V$ is determined, the numerical derivative of the heat capacity $C_V$ with respect to the density $\rho$ at constant temperature, denoted as $$\left(\frac{\partial C_V}{\partial \rho}\right)_T,$$

is determined. The numerical derivative $$\left(\frac{\partial C_V}{\partial \rho}\right)_T$$

may be expressed as $$\left(\frac{\partial C_V}{\partial \rho}\right)_T = \frac{C_V(\rho + \Delta\rho, T) - C_V(\rho - \Delta\rho, T)}{2\Delta\rho}.$$

Generally, the numerical derivative may be calculated from measurements at an isochore both above and below the current isochore as known to those skilled in the art.

Once the numerical derivative $$\left(\frac{\partial C_V}{\partial \rho}\right)_T$$

is known, then a solution may be found for $$\left(\frac{\partial^2 Z}{\partial T^2}\right)_\rho$$

using equation 2.13 which, once again is expressed as $$\left(\frac{\partial^2 Z}{\partial T^2}\right)_\rho = -\frac{\frac{\rho}{R}\left(\frac{\partial C_V}{\partial \rho}\right)_T + 2T\left(\frac{\partial Z}{\partial T}\right)_\rho}{T^2},$$

where R is the universal gas constant.

Finally, new values for the compressibility Z and the partial derivative $$\left(\frac{\partial Z}{\partial T}\right)_\rho$$

are found with the variables determined above using the Taylor series approximations of equations 2.14 and 2.15 denoted as $$Z_{NEW} = Z + \Delta T\left(\frac{\partial Z}{\partial T}\right)_\rho + \frac{1}{2}\Delta T^2\left(\frac{\partial^2 Z}{\partial T^2}\right)_\rho, \text{ and} \quad 2.14$$

$$\left[\left(\frac{\partial Z}{\partial T}\right)_\rho\right]_{NEW} = \left(\frac{\partial Z}{\partial T}\right)_\rho + \Delta T\left(\frac{\partial^2 Z}{\partial T^2}\right)_\rho. \quad 2.15$$

The new values for the compressibility Z and the partial derivative $$\left(\frac{\partial Z}{\partial T}\right)_\rho$$

are more accurate than the originally estimated initial values. A new, more accurate value for the density p may then be calculated from the compressibility Z as known by those skilled in the art. The foregoing calculations are repeated at the next $\Delta T$, using the new measurements for the temperature T, the speed of sound u, and pressure P and the new values for the compressibility Z, the partial derivative $$\left(\frac{\partial Z}{\partial T}\right)_\rho,$$

and the density $\rho$ previously calculated. This process is repeated for each $\Delta T$, causing the heat capacity $C_V$, the compressibility Z, and the partial derivative $$\left(\frac{\partial Z}{\partial T}\right)_\rho$$

to converge to their actual values. Also, the density p which is calculated from these parameters in turn becomes more accurate.

The calculation of the compressibility Z, partial derivative $$\left(\frac{\partial Z}{\partial T}\right)_\rho,$$

and density $\rho$ across a single specified temperature range makes a single iteration. The value for the density $\rho$ that results from a single iteration may be used as the initial value (previously estimated) of the density $\rho$ for a second iteration which is performed based on the same measured values for the temperature T, pressure P, and speed of sound u at the same temperature intervals of $\Delta T$. The initial values for the compressibility Z and the partial derivative $$\left(\frac{\partial Z}{\partial T}\right)$$

may be estimated again based on the new value of the density $\rho$. In this fashion, several iterations are possible, each of which will cause the density $\rho$, the compressibility Z and the partial derivative $$\left(\frac{\partial Z}{\partial T}\right)$$

to converge on their actual values. The total number of iterations that may be performed are those necessary to achieve the desired accuracy of the calculated parameters.

After accurate values for the density $\rho$, heat capacity $C_V$, the compressibility Z, and the partial derivative $$\left(\frac{\partial Z}{\partial T}\right)_\rho$$

have been determined, other thermophysical properties are then calculated from these properties using various thermophysical equations as known by those skilled in the art. These properties would include the compressibility factor, the heat capacity, entropy, enthalpy, free energy, internal energy and other related properties.

Turning to FIG. 1, shown is a measuring system 50 employed in performing the method of the instant invention. Shown is a vessel 53 containing a volume of the medium 56. The medium 56 is generally in the form of a gas that conforms to the laws of thermophysicals as known by those skilled in the art. Attached to the vessel 53 and in physical contact with the medium 56 are pressure transducer 59, temperature probe 62, sonic transducer 65, temperature control device 68, solenoid valve 69, and agitation device 71.

The instant invention also features computer system 73 which houses the central processing unit ("CPU") 74 and the computer memory 77. The CPU 74 operates pursuant to the isochoric operating software 80 stored in computer memory 77. Data bus 83 links the CPU 74 with the computer memory 77. It must be noted that a dedicated electronic system may be created to perform the tasks accomplished by the CPU 74 in conjunction with the computer memory 77 and the isochoric operating software 80, rather than a generic microprocessor based computing system as contemplated by the first embodiment here as is known to those skilled in the art.

Also coupled to the data bus 83 are the pressure transducer interface 86, temperature probe interface 89, sonic transducer interface 92, temperature control interface 95, and a solenoid valve interface 96. The pressure transducer interface 86 generally accepts an analog input that converts an analog pressure signal into a digital signal that may be processed by the CPU 74 as known to those skilled in the art. The pressure transducer 59 is electrically coupled to the pressure transducer interface 86 to provide the analog pressure signal to the pressure transducer interface 86. It would be possible that the signal be in digital form as well.

Likewise, the temperature probe interface 89 is electrically coupled to the temperature probe 62, and generally accepts an analog temperature signal from the temperature probe 62. It would also be possible that the temperature signal be in digital form.

The sonic transducer interface 92 is coupled to the sonic transducer 65 and comprises higher order electronics to perform the specific functions necessary to obtain the speed of sound as known to one skilled in the art. In particular, the sonic transducer 65 is capable of creating a sonic pulse 97 pursuant to a signal from the sonic transducer interface 92 which travels through the medium 56 reflecting off of the wall of the vessel 53. A "sonic" transducer as contemplated herein refers to any transducer that can create and detect any sound wave at any frequency. An example of the type of sonic transducer as contemplated herein would be that described in U.S. Pat. No. 5,600,610 filed on Jan. 31, 1995, entitled "Electrostatic Transducer and Method for Manufacturing Same," the entire text of which is incorporated herein by reference.

A reflected pulse 99 then propagates back toward the sonic transducer 92 where it is detected by sonic transducer 65. There are multiple different electrical configurations such as the sonic transducer interface 92 and the sonic transducer 65 that may be employed as known to those skilled in the art. This method of obtaining the speed of sound is commonly referred to as the "time of flight" method. Note that the transducers may be placed in several different configurations to obtain the speed of sound via the time of flight method as known to those skilled in the art. Also other methods include the resonance method and the ringdown method as know to those skilled in the art. All may be employed to determine the speed of sound according to the instant invention.

The temperature control interface 95 is electrically coupled to the temperature control device 68. In the first embodiment, the temperature control interface 95 is an analog output module which will provide a signal proportional to the temperature desired in the vessel 53 based on a digital signal received from the CPU 74 over the data bus 83 as known to those skilled in the art. The temperature control device is capable of both heating and cooling the medium at the direction of the CPU 74 being controlled by a feedback loop resident in the temperature control device 69 as known by those skilled in the art. It would also be possible that the temperature control interface only provide discrete signals that activate heating or cooling devices in the temperature control device, using the temperature measurement from the temperature probe 62 for temperature feedback.

The valve control interface 86 is electrically coupled to the solenoid valve 69, providing a discrete voltage or current signal which causes the solenoid valve 69 to open or close as known by those skilled in the art. In the first embodiment, the flow of the medium 56 through the solenoid valve out of the vessel 53 may be adjusted as is customary in the art. Also in the first embodiment, the medium 56 is held at a higher pressure than the area into which the solenoid valve 69 directs the medium 56 so as to ensure flow out of the vessel 53.

The agitation device 71 consists mainly of a fan blade and is used to constantly stir up the medium 56 to maintain a uniform mixture throughout the vessel 53. However, device other than a fan blade may be used as is customary in the art.

Figure 2:
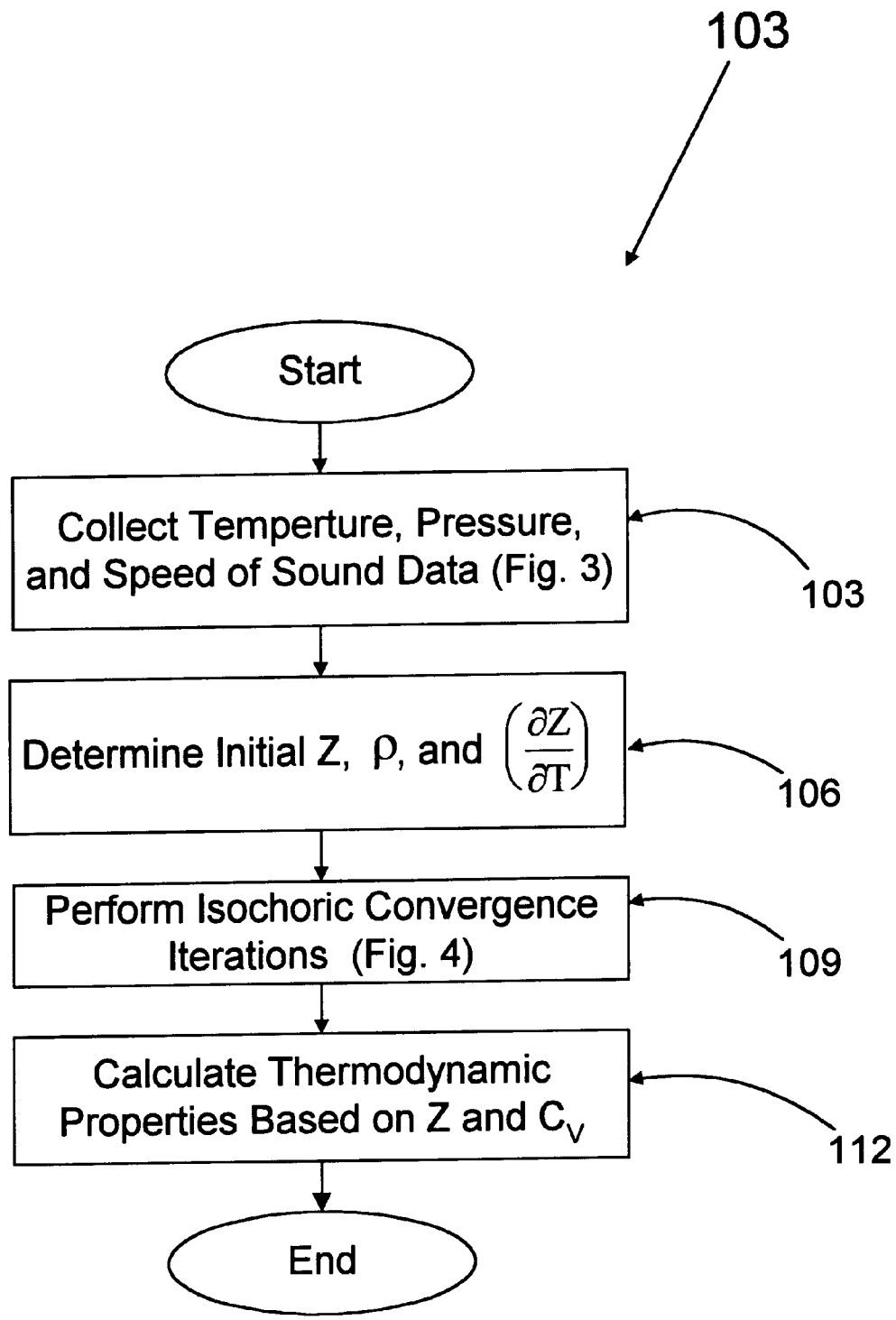
FIG. 2 is a flow diagram illustrating the method according to the first embodiment of the invention shown in FIG. 1.

Turning to FIG. 2, shown is a flow diagram of the isochoric operating software 80 which performs the steps of the instant invention according to the first embodiment. In step 103, the temperature, pressure, and speed of sound data are collected with which to perform the convergence calculations. Later discussion describes a flow chart that further defines this step. In step 106, initial values for z, $\rho$, and $$\left(\frac{\partial Z}{\partial T}\right)_\rho$$

are determined as previously described to be used in the first iteration. These values are then stored in memory for future use in later calculation. Once the initial values are ascertained, in step 109, the isochoric convergence iterations are performed to obtain accurate values of the heat capacity $C_V$, density $\rho$, and the compressibility Z. Later discussion will include a description of flow charts that further define this step. Finally, in step 112, the general thermophysical properties are calculated based upon the heat capacity $C_V$, density $\rho$, and the compressibility Z that are ultimately determined.

Figure 3:
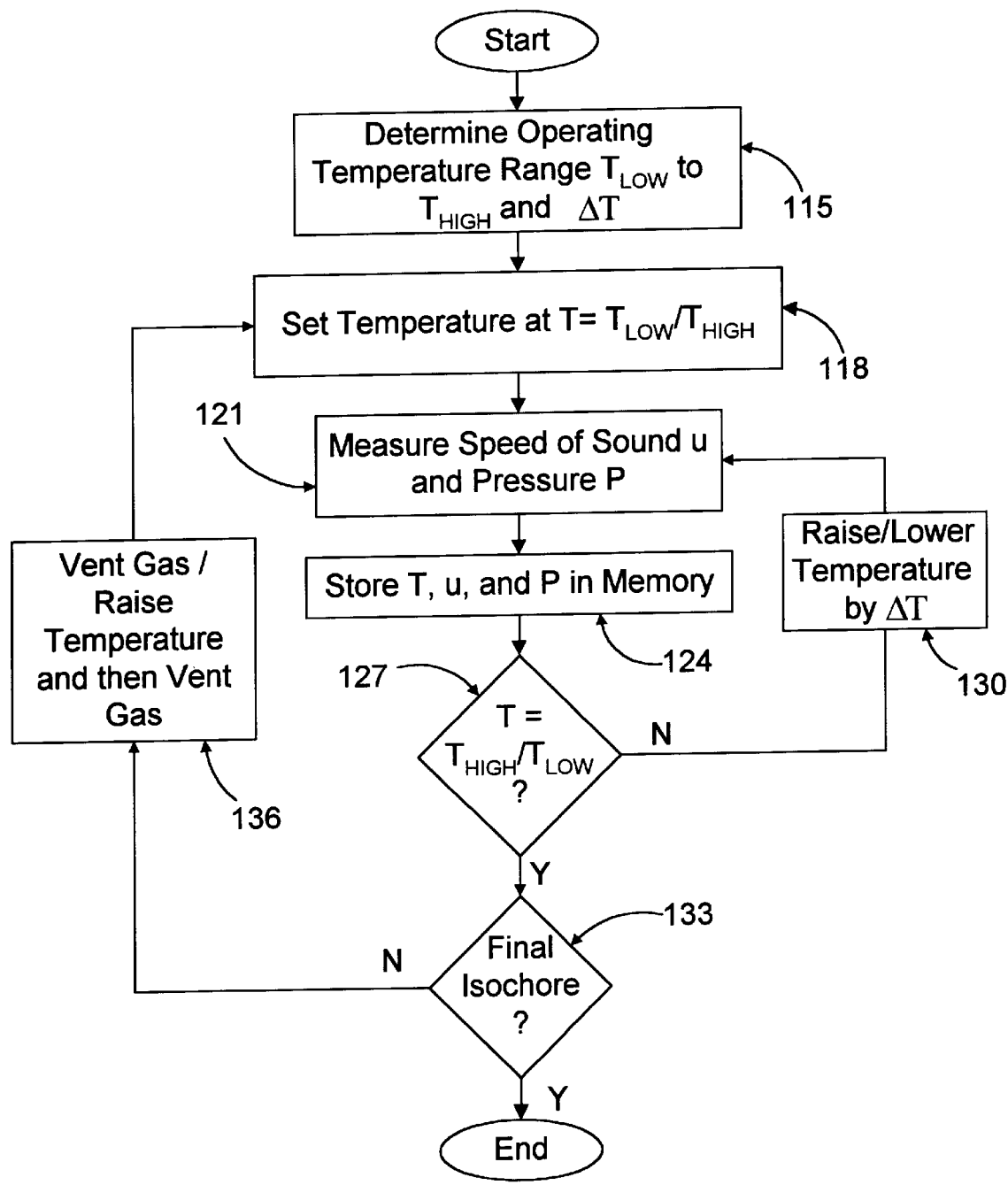
FIG. 3 is a flow diagram illustrating the method of accomplishing the data acquisition step of FIG. 2.

Referring to FIG. 3, shown is a flow chart that outlines the steps encompassed in acquiring the temperature, pressure, and speed of sound data of step 103 (FIG. 2). In step 115, the operating temperature range $T_{LOW}$ or $T_{HIGH}$ and $\Delta T$ are determined. In the first embodiment, a suggested operating temperature range may be generally equal to a span of approximately 100° K., although a greater or lesser temperature range may be specified. In the first embodiment, the suggested value of $\Delta T$ is approximately 0.5° K. This number may be greater and then lower values of $\Delta T$ may be interpolated from the larger intervals taken.

Next, in step 118, the temperature of the medium 56 (FIG. 1) is brought to the beginning temperature of the range which may be either $T_{LOW}$ or $T_{HIGH}$. It would be preferable to use $T_{HIGH}$ as the starting temperature to ensure a uniform mixture of the medium where no component is near its liquid stage. To accomplish this step, the temperature control 95 (FIG. 1) is activated by the CPU 74 (FIG. 1) as known by those skilled in the art.

In step 121 the speed of sound u and the pressure P of the medium 56 are measured. Turning back to FIG. 1, the pressure P is measured using the pressure transducer 59 as known by those skilled in the art. The speed of sound is measured using the sonic transducer 65. Specifically, the sonic transducer interface 92 generates and sends and electrical pulse to the sonic transducer 65. The sonic transducer 65 generates a sonic pulse 97 based on this electrical pulse which travels across the medium, striking the wall of the vessel 53 opposite the sonic transducer 65. A reflected sonic pulse 99 then propagates back toward the sonic transducer 65. The reflected sonic pulse 99 is detected by the sonic transducer 65 which sends an electrical signal back to the sonic transducer interface 92. A timer that was initiated when the first electrical pulse was generated will be stopped, giving the time the pulse traveled across the medium 56. The speed of sound is determined by dividing the distance traveled by the sonic pulses 97 and 99 by the total travel time. The determination of the speed of sound in medium 56 as such is an expedient within the understanding of one skilled in the art.

Turning back to FIG. 3, in step 124, the values for the temperature T, speed of sound u, and pressure P are stored in a table which may be accessed by the convergence step 109 (FIG. 2). Next in step 127, in the case where the starting temperature chosen in step 118 was $T_{HIGH}$, the current temperature T is compared with the $T_{LOW}$. If the temperature T is greater than $T_{LOW}$, then step 130 is implemented in which the temperature T is lowered by $\Delta T$. On the other hand, if the starting temperature chosen in step 118 was $T_{LOW}$, the current temperature T is compared with $T_{HIGH}$. If the temperature T is less than $T_{HIGH}$, then step 130 is implemented in which the temperature T is raised by $\Delta T$. In either case, after the temperature T is adjusted, step 121 is executed in which the speed of sound u and pressure P are measured once again. This loop will repeat itself until the speed of sound u and pressure P have been measured for all temperature increments in the operating temperature range specified. If in step 127, the temperature finally reaches $T_{HIGH}$ or $T_{LOW}$, which ever the case may be, the next step 133 is implemented.

In step 133 the determination is made as to whether the above measurements are to be performed on another isochore. In the first embodiment, three isochores are measured in which the densities vary by approximately 0.5 mol/liter. Although this variation may be larger or smaller, the accuracy of the numerical derivatives may be compromised if it is too large or too small. The data taken for the two isochores with the lowest and highest densities is used to determine the numerical derivatives as discussed previously. It would be possible to determine these numerical derivatives without taking more than one isochore as taking a numerical derivative is well known to those skilled in the art.

In the case of the first embodiment, in step 133, the determination is made as to whether the final isochore has been taken. If it has not, then in step 136 an amount of the medium is vented from the vessel 53 (FIG. 1). Note if the starting temperature selected in step 118 was $T_{LOW}$, then in step 136 the solenoid valve 69 (FIG. 1) is simply forced open by the valve control interface 96 (FIG. 1) to allow some of the medium 56 to vent from the vessel 53. This is due to the fact that the current temperature of the medium is $T_{HIGH}$ thereby ensuring that the medium is uniform and that no component is in a liquid state. On the other hand, if the starting temperature selected in step 118 was $T_{HIGH}$, then in step 136, the temperature of the medium 56 is first raised to $T_{HIGH}$ and then the solenoid valve 69 is opened and the venting takes place. Ultimately, the goal is to ensure that no venting takes place at a temperature in which any component of the multi-component medium is at or near a liquid state. If it is known that this is not the case at a temperature of $T_{LOW}$, then the venting may occur at that temperature as well.

Additionally, the flow of the medium 56 through the valve 69 is controlled so that it is not too great so as to prevent a drastic change in the density. After the density is adjusted as such, step 118 is implemented and the data acquisition begins on the new isochore. In this case, step 118 will set the temperature T to equal $T_{LOW}$ or $T_{HIGH}$, whichever is preferable. If both may be used, then one may alternate starting temperatures at step 118 to save on heating and cooling costs. If the final isochore has been taken in step 133, then the data acquisition step 130 ends.

Figure 4:
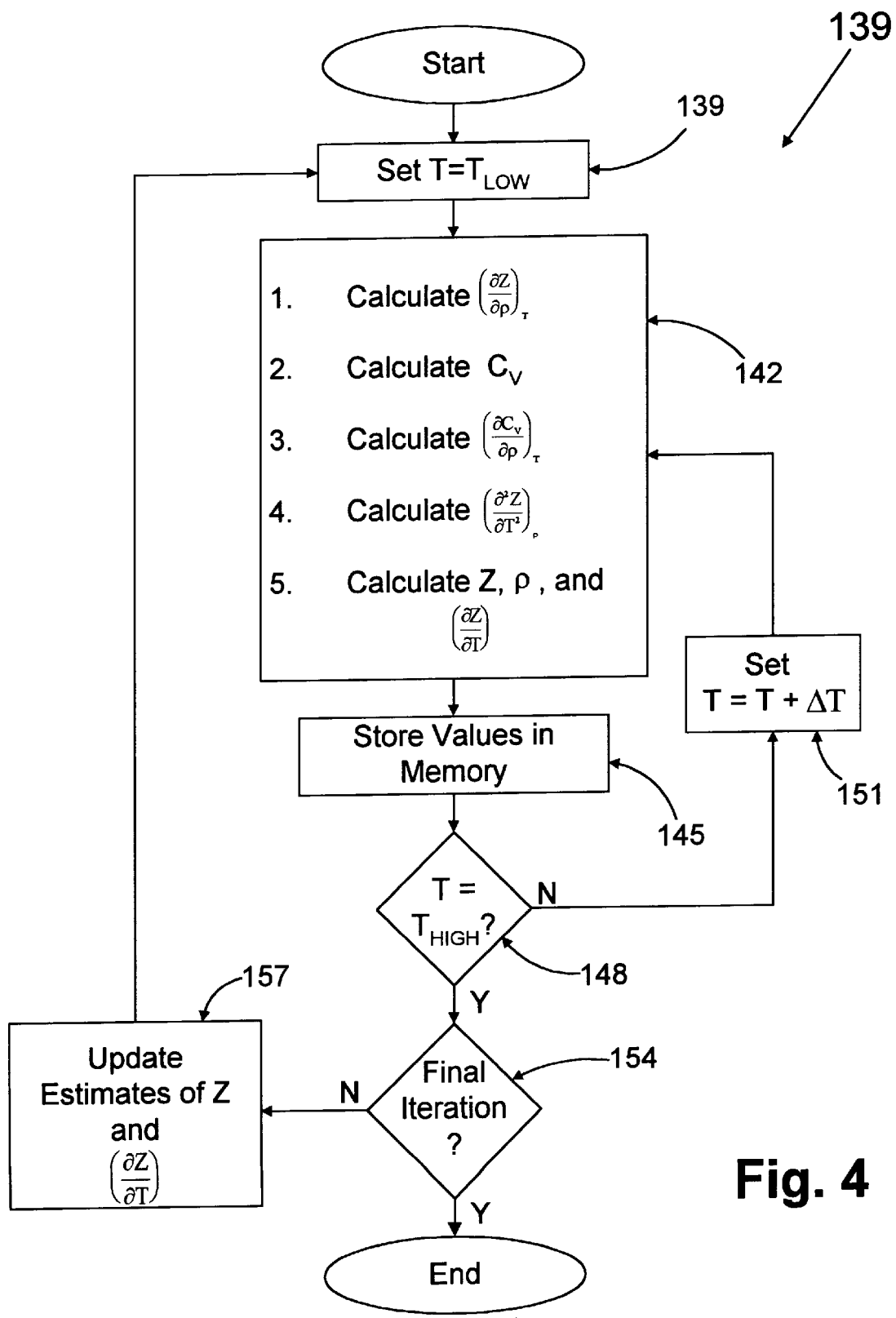
FIG. 4 is a flow diagram illustrating the method of accomplishing the isochoric convergence step of FIG. 2.

Referring now to FIG. 4, shown is a flow chart which illustrates the steps taken during the isochoric convergence of step 109 (FIG. 2) according to the first embodiment. In step 139, the temperature variable is set to equal the lowest temperature value in the range of temperatures at which the speed of sound u and the pressure P were measured. The temperature variable T is used as a pointer in this context, causing the access to the correlating temperature, speed of sound and pressure data for a specific temperature increment.

In the next step, the listed progression of calculations previously discussed is executed. When this step is performed for the first time for a particular isochore, the initial values of the density $\rho$, compressibility Z, and $\left(\frac{\partial Z}{\partial T}\right)$ determined in step 106 (FIG. 2) are used in the calculations. Subsequent to the first time step 142 is performed, the density ρ, compressibility Z, and $\left(\frac{\partial Z}{\partial T}\right)$ calculated from previous calculations are used. The actual calculations performed include the numerical derivative $\left(\frac{\partial Z}{\partial \rho}\right)_T$, the heat capacity $C_V$, the numerical derivative $\left(\frac{\partial C_V}{\partial \rho}\right)_T$, the second derivative $\left(\frac{\partial^2 Z}{\partial T^2}\right)_\rho$, and finally new values for the compressibility Z, density ρ, and the numerical derivative $\left(\frac{\partial Z}{\partial T}\right)$.

In step 145, the resulting values for Z, ρ, and $\left(\frac{\partial Z}{\partial T}\right)$ are then stored in memory for use in subsequent calculation.

In step 148, an inquiry is made to determine whether the value of the temperature variable T has surpassed the highest temperature $T_{HIGH}$ measured in the specified operating temperature range. If this is not the case then step 151 is executed in which the temperature variable T is incremented by ΔT and the calculations of step 142 are repeated at the new temperature T. Note that the values for compressibility Z, density ρ, and the numerical derivative $\left(\frac{\partial Z}{\partial T}\right)$ resulting from the previous execution of step 142 are used in the current calculations of this step. Each time step 142 is executed, these values will converge to their actual values. In this way an estimate of these parameters is used to start with, and according to the method of the first embodiment, precise values are obtained.

If in step 148, the temperature variable T is greater than $T_{HIGH}$, step 154 is then executed. At this point the determination is made as to whether further iterations are necessary to gain greater accuracy of compressibility Z, density ρ, and the numerical derivative $\left(\frac{\partial Z}{\partial T}\right)$.

The calculation of these variables over the specified temperature range is defined as a single iteration. If another iteration is desired, then value of the density ρ determined in the final execution of step 142 is used as the initial density ρ for the next iteration. Also, in step 157, new estimates of the initial values of the compressibility Z and the numerical derivative $\left(\frac{\partial Z}{\partial T}\right)$ may be calculated or otherwise determined based on the new initial density ρ. In such a case the step 157 would include the necessary calculations employed to estimate the compressibility and the numerical derivative $\left(\frac{\partial Z}{\partial T}\right)$ as estimating these values based on the density ρ is known in the art. The execution then reverts to step 139 in which another iteration is then performed. If in step 154, another iteration is not desired, then the isochoric convergence is complete and the execution comes to an end.

Convergence Using Isobaric Equations

In the following discussion, the second embodiment of the present invention is described in which the formulas derived above relating to the isobaric speed of sound equations are employed to ascertain accurate thermophysical properties of a multi-component gas medium.

To begin, a temperature range is specified over which measurements of the speed of sound of the particular volume of multi-component medium will be taken. Also, a temperature step ΔT is chosen at which to take these measurement across the range specified. Note that, as previously mentioned, the temperature step ΔT need not be uniform across the temperature range. Uniformity may be achieved by interpolation techniques as known to those skilled in the art.

Next, the temperature of the medium is brought to either the low end, $T_{LOW}$, or the high end, $T_{HIGH}$, of the temperature range to begin taking measurements of physical parameters. Since the isobaric convergence discussed herein does not require venting of the medium as is the case of isochoric convergence discussed previously, the choice of whether to start at $T_{HIGH}$ or $T_{LOW}$ is arbitrary. In the case where $T_{LOW}$ is chosen as to start, the temperature of the medium is then raised in steps by ΔT. In the case where $T_{HIGH}$ is chosen as to start, the temperature of the medium is lowered in steps by ΔT. In either case, at each step the speed of sound u of the medium is measured. This cycle of raising or lowering the temperature in steps of ΔT and measuring the speed of sound at each step is continued until measurements have been taken across the entire specified temperature range. In the second embodiment, the temperature T and speed of sound u for each temperature increment are stored in memory for further evaluation. During the entire process, the pressure P is kept as constant as is possible.

After the values of the speed of sound have been determined for each interval across the specified temperature range, a process based on the measurement of the speed of sound, pressure, and temperature is undertaken in which the thermophysical properties of the multi-component medium are ascertained. According to the second embodiment, new and more accurate values for the compressibility Z and $$\left(\frac{\partial Z}{\partial T}\right)$$

are calculated for each $\Delta T$ using the Z and $$\left(\frac{\partial Z}{\partial T}\right)$$

from the previous calculation, thereby converging on more precise values for these properties across the specified temperature range. For the first calculation at the first $\Delta T$, an estimate of the Z and $$\left(\frac{\partial Z}{\partial T}\right)$$

are used as initial values.

The first step in isobaric convergence is to determine initial values for the compressibility Z and $$\left(\frac{\partial Z}{\partial T}\right).$$

. These values are estimated in the same manner as was described for the isochoric convergence of the first embodiment.

Once values for each of these variables are obtained, the numerical derivative of the initial compressibility Z with respect to pressure P at constant temperature, denoted as $$\left(\frac{\partial Z}{\partial P}\right)_T,$$

is determined. The numerical derivative may be expressed as $$\left(\frac{\partial Z}{\partial P}\right)_T = \frac{Z(P + \Delta P, T) - Z(P - \Delta P, T)}{2\Delta P}.$$

Generally, the calculation of the numerical derivative may be performed based on physical measurements at an isobar both above and below the current isobar as known to those skilled in the art. There are also other methods of determining the numerical derivative as known in the art.

Next, the isobaric heat capacity $C_P$ is found using previously derived equation 3.12 which, once again, is expressed as $$C_P = \frac{R\left[Z + T\left(\frac{\partial Z}{\partial T}\right)_P\right]^2}{u^{-2}\left(\frac{RTZ^2}{M}\right) - Z + P\left(\frac{\partial Z}{\partial P}\right)_T}, \quad 3.12$$

where M is the molecular mass and R is the universal gas constant.

Once the isobaric heat capacity $C_P$ is determined, the numerical derivative of the heat capacity $C_P$ with respect to the pressure P at constant temperature, denoted as $$\left(\frac{\partial C_P}{\partial P}\right)_T,$$

is determined. The numerical derivative $$\left(\frac{\partial C_P}{\partial P}\right)_T$$

may be expressed as $$\left(\frac{\partial C_P}{\partial P}\right)_T = \frac{C_P(P + \Delta P, T) - C_P(P - \Delta P, T)}{2\Delta P}.$$

As before, the numerical derivative may be calculated from measurements at an isobar both above and below the current isobar or by other methods as known to those skilled in the art.

Once the numerical derivative $$\left(\frac{\partial C_P}{\partial P}\right)_T$$

is known, then a solution may be found for $$\left(\frac{\partial^2 Z}{\partial T^2}\right)_P$$

using equation 3.13 which, once again is expressed as $$\left(\frac{\partial^2 Z}{\partial T^2}\right)_P = -\frac{\frac{P}{R}\left(\frac{\partial C_P}{\partial P}\right)_T + 2T\left(\frac{\partial Z}{\partial T}\right)_P}{T^2}. \quad 3.13$$

where R is the universal gas constant.

Finally, new values for the compressibility Z and the partial derivative $$\left(\frac{\partial Z}{\partial T}\right)_P$$

are found with the variables determined above using the Taylor series approximations of equations 3.14 and 3.15 denoted as $$Z_{NEW} = Z + \Delta T\left(\frac{\partial Z}{\partial T}\right)_P + \frac{1}{2}\Delta T^2\left(\frac{\partial^2 Z}{\partial T^2}\right)_P, \text{ and} \quad 3.14$$

$$\left[\left(\frac{\partial Z}{\partial T}\right)_P\right]_{NEW} = \left(\frac{\partial Z}{\partial T}\right)_P + \Delta T\left(\frac{\partial^2 Z}{\partial T^2}\right)_P. \quad 3.15$$

As was the case with the isochoric conversion, the new values for the compressibility Z, the isobaric heat capacity $C_P$, and the partial derivative $$\left(\frac{\partial Z}{\partial T}\right)_P$$

are more accurate than the originally estimated initial values. The foregoing calculations are then repeated at the next $\Delta T$ using the new measurements for the temperature T, speed of sound u, and pressure P and the new values for the compressibility Z and the partial derivative $$\left(\frac{\partial Z}{\partial T}\right)_P$$

calculated previously. This process is repeated for each $\Delta T$, causing the heat capacity CP, compressibility Z, and partial derivative $$\left(\frac{\partial Z}{\partial T}\right)_P$$

to converge to their actual values.

The isobaric convergence differs from the isochoric convergence in that a single iteration is performed. Consequently, the convergence of the above parameters using the second embodiment of the present invention provides a lesser degree of accuracy than the isochoric equations.

As was the case with isochoric convergence, other thermophysical properties including those listed may be calculated using the heat capacity $C_P$ and the compressibility Z as known by those skilled in the art.

It must be noted that the isobaric approach described above is very close to an isothermal approach in that if enough isobars are taken, the pressure, temperature, and speed of sound data would be identical if isothermal measurements were taken at isotherms corresponding to each $\Delta T$. That is to say, the same data can be produced by varying the pressure by intervals of $\Delta P$ at a constant temperature. Consequently, although the convergence is termed isobaric, it can also be labeled as isothermal.

Figure 5:
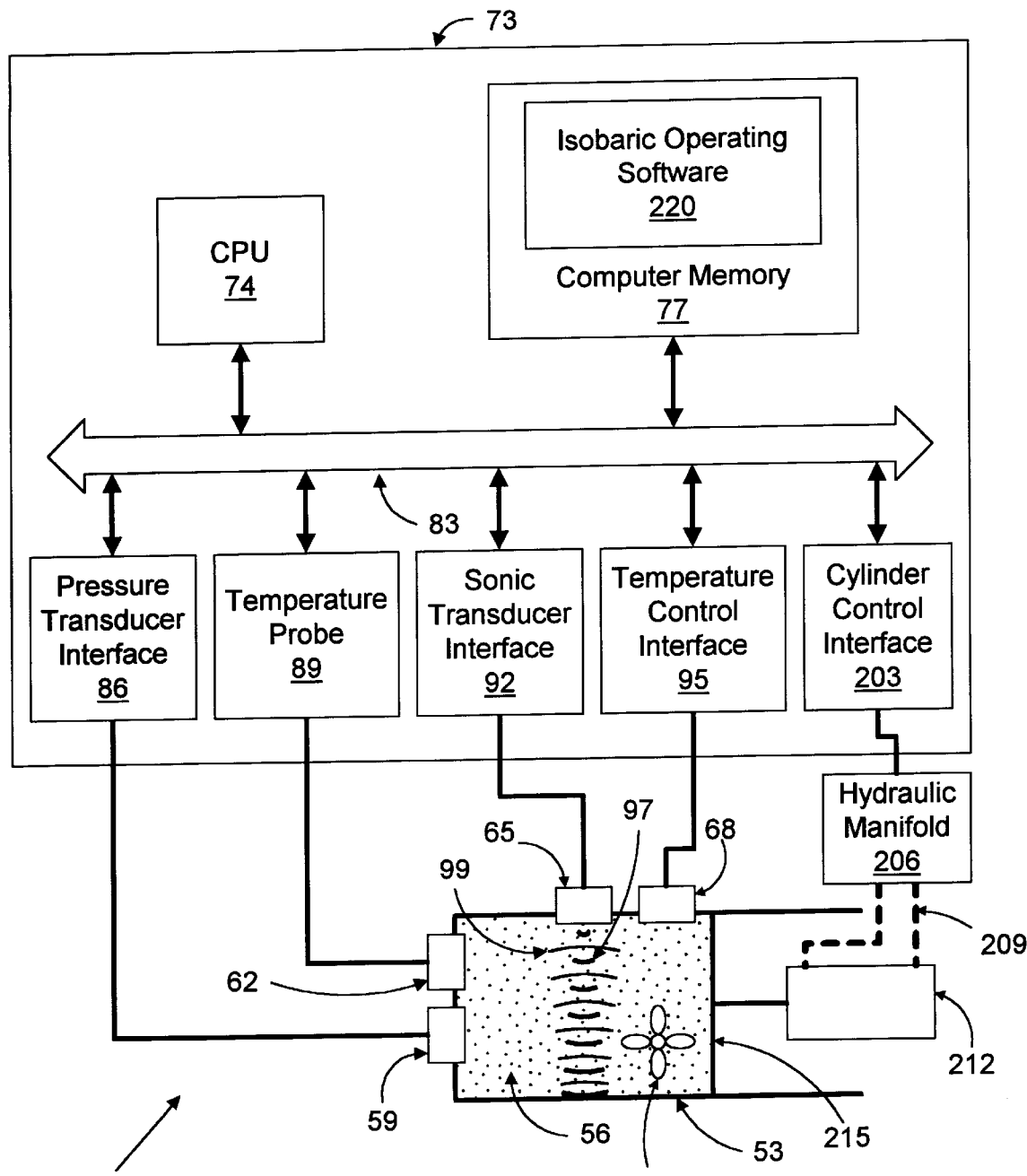
FIG. 5 is a drawing illustrating an system used in performing the method according to the second embodiment of the instant invention.

Turning then to FIG. 5, shown is a measuring system 200 employed in performing the second embodiment of the present invention. The measuring system 200 is nearly identical to the measuring system 50 (FIG. 1) with virtually the same components, with the following exceptions. The measuring system 200 does not include the solenoid valve 69 (FIG. 1) or the valve control interface (FIG. 1). Instead, the measuring system 200 includes the cylinder control interface 203 which is electrically connected to solenoid valves on the hydraulic manifold 206. Hoses 209 allow hydraulic fluid to reach the hydraulic cylinder 212 which in turn moves the plunger 215 back and forth, thereby changing the volume of the vessel 53.

By changing the volume of the vessel 53, the pressure P of the medium 56 is controlled. In the second embodiment of the invention, the cylinder control interface 203 provides discrete voltage signals to trigger solenoid valves on the hydraulic manifold 206. The control of a hydraulic cylinder as contemplated herein is well known to those skilled in the art. Also, the CPU 74 operates according to the isobaric operating software 220 which differs from the isochoric operating software 80. The operation of the measuring system 200 is generally the same as the measuring system 50 (FIG. 1), with the exception of the isobaric operating software 220 and the control of the volume of the vessel 53 via the hydraulic cylinder 212 which is described in detail in the paragraphs that follow.

Note that the vessel 53 may be constructed with a variable volume, such as an accordian type of enclosure as known in the art. Also, the volume may be varied by incorporating a moveable wall of the vessel 53 that is in contact with the vessel via seals as known by those skilled in the art. Generally, any method of varying the volume of a particular vessel 53 customary in the art will suffice.

Also note that the vessel 53 of variable volume may be used in the first embodiment as an alternative to the solenoid valve 69 (FIG. 1). In effect, one may alter the density by altering the volume as known in the art. In such a case, in step 136 (FIG. 3) the volume would be adjusted as is the case with the second embodiment of the invention as shown in FIG. 5.

Figure 6:
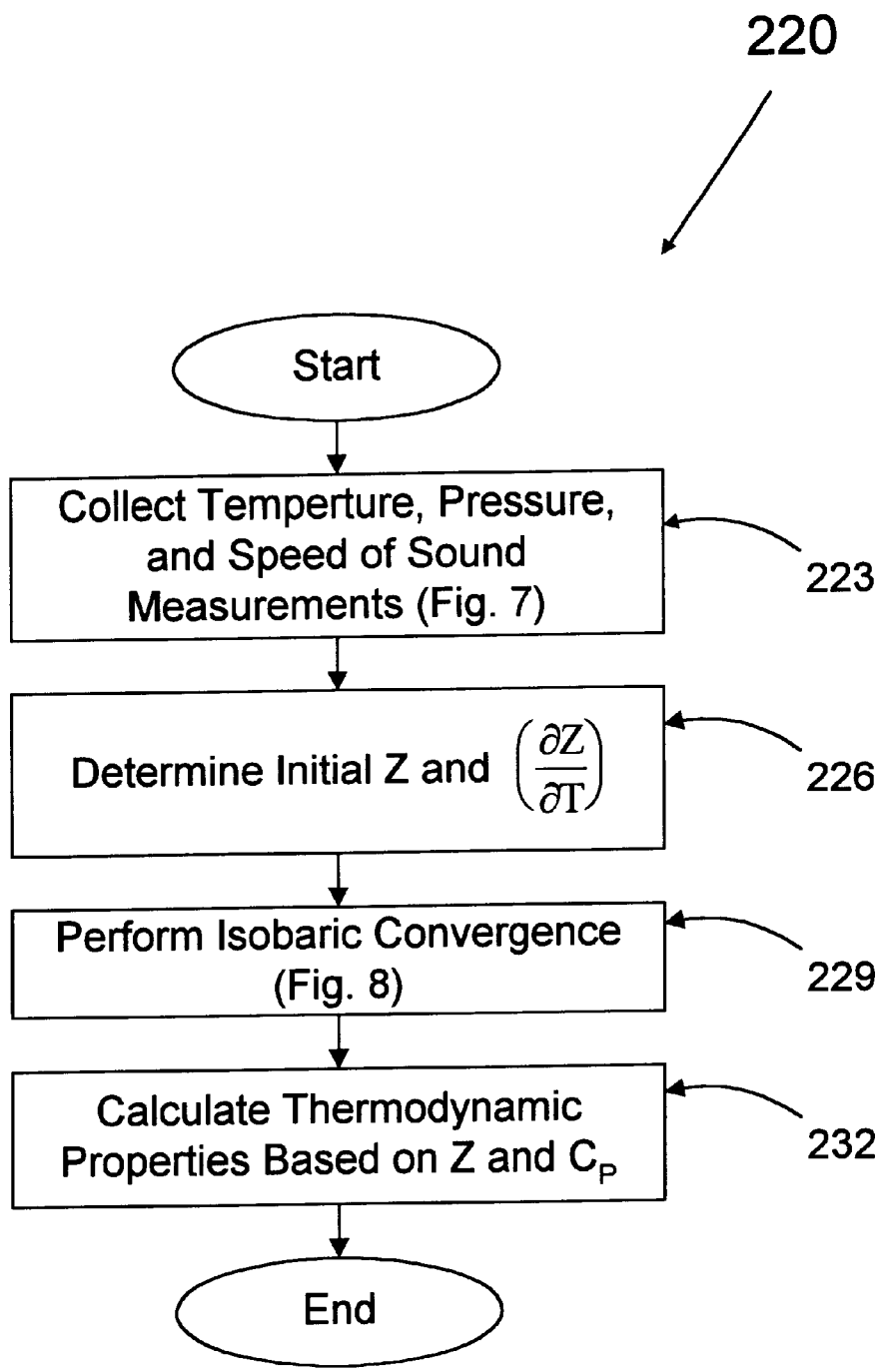
FIG. 6 is a flow diagram illustrating the method according to the second embodiment of the invention shown in FIG. 5.

Turning now to FIG. 6, shown is a flow diagram of the isobaric operating software 220 which performs the steps of the instant invention according to the second embodiment. In step 223, the temperature, pressure, and speed of sound data are collected with which to perform the convergence calculations. Later discussion describes a flow chart that further defines this step. In step 226, initial values for Z and $$\left(\frac{\partial Z}{\partial T}\right)$$

are determined as previously described to be used in the first iteration. Once the initial values are ascertained, in step 229, the isobaric convergence calculations are performed to obtain accurate values of the heat capacity $C_P$ and the compressibility Z. Later discussion will include a description of flow charts that further define this step. Finally, in step 332, the general thermophysical properties are calculated based upon the heat capacity $C_P$ and the compressibility Z that are ultimately determined. The calculation of the general thermophysical properties as such is well those skilled in the art.

Figure 7:
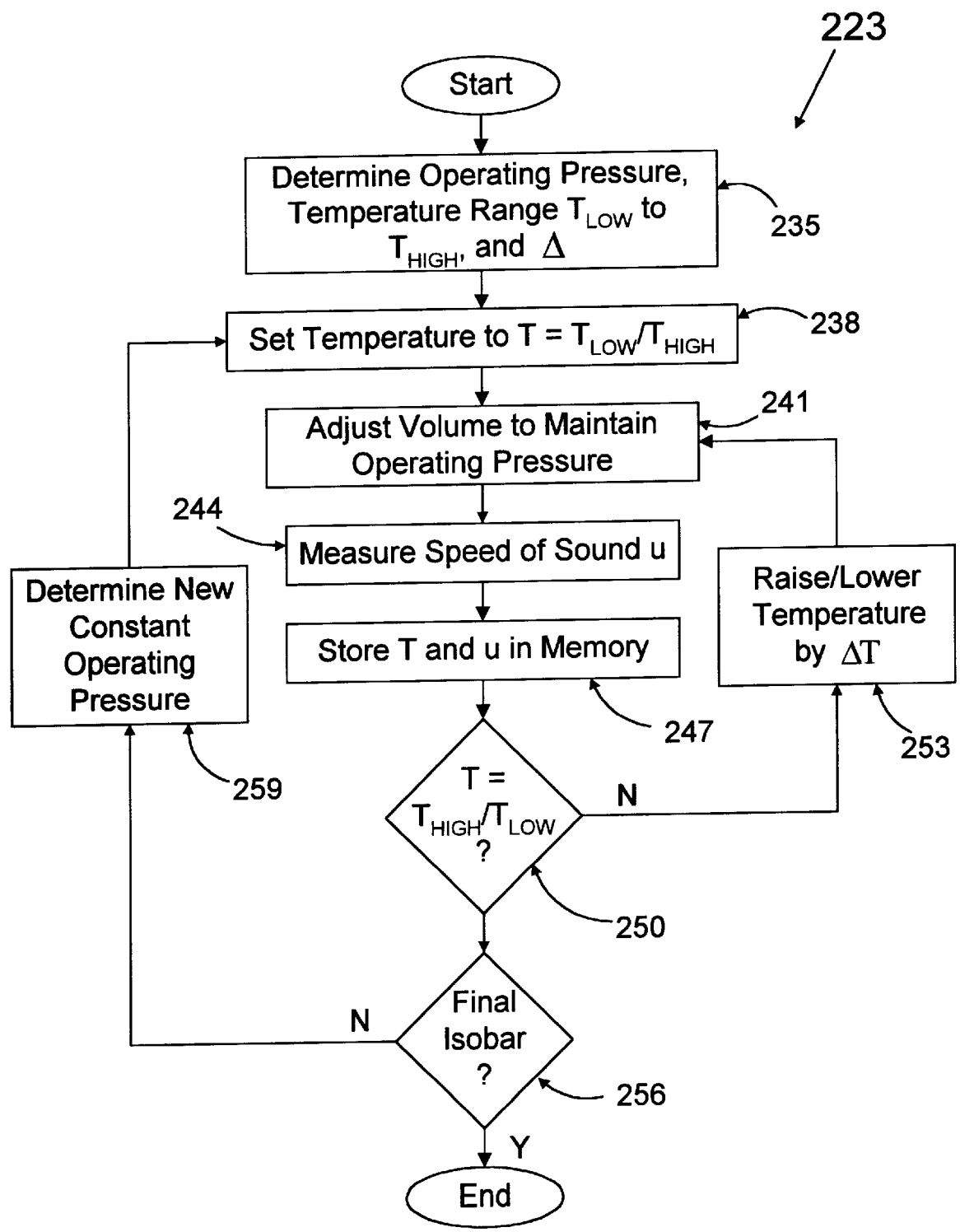
FIG. 7 is a flow diagram illustrating the method of accomplishing the data acquisition step of FIG. 6.

Referring to FIG. 7, shown is a flow chart that outlines the steps encompassed in acquiring the speed of sound data at the temperature steps $\Delta T$ at constant pressure P of step 223 (FIG. 6). In step 235, the operating temperature range $T_{LOW}$ to $T_{HIGH}$, constant pressure P and $\Delta T$ are determined. As was the case with the first embodiment, a suggested operating temperature range may be generally equal to a span of approximately 100° K., although a greater or lesser temperature range may be employed. Also, as with the first embodiment, the suggested value of $\Delta T$ is approximately 0.5° K. This number may be greater, and then lower values of $\Delta T$ may be interpolated from the larger intervals taken.

Next, in step 238, the temperature of the medium 56 (FIG. 5) is brought to the beginning temperature of the range which may be $T_{LOW}$ or $T_{HIGH}$. To accomplish this step, the temperature control 95 (FIG. 5) is activated by the CPU 74 (FIG. 5) as known by those skilled in the art.

In step 241, the volume of the vessel 53 (FIG. 5) is adjusted so that the operating pressure P of the medium 56 (FIG. 5) is maintained. The pressure P is changed due to the rise in temperature as known to those skilled in the art. The adjustment is accomplished by causing the cylinder 212 (FIG. 5) to extend or retract as needed, using the pressure transducer 59 (FIG. 5) for pressure feedback. Adjusting the volume as such to maintain the constant operating pressure is an expedient known to those skilled in the art.

Next, in step 244 the speed of sound u of the medium 56 (FIG. 5) is measured. The speed of sound in the case of isobaric convergence is accomplished in the same manner as was the case with isochoric convergence, and as such, will not be discussed in detail.

Moving on to step 247, the values for the temperature T, speed of sound u, and constant operating pressure P are stored in a table which may be accessed by the convergence step of step 229 (FIG. 6). Next, in step 250, the current temperature T is compared with $T_{HIGH}$ or $T_{LOW}$, depending on which was chosen as a starting temperature at step 238. If $T_{HIGH}$ was chosen at step 238, then step 253 is implemented if the temperature T at step 250 is greater than $T_{LOW}$. In such a case the temperature T is lowered by $\Delta T$ at step 253. If $T_{LOW}$ was chosen at step 238, then step 253 is implemented if the temperature T at step 250 is less than $T_{HIGH}$. In this situation, the temperature T is raised by $\Delta T$. In either case, step 241 is performed after the execution of step 253 where the constant pressure P is maintained. This loop will repeat itself until the speed of sound u has been measured for all temperature increments in the operating temperature range specified. If in step 250, the temperature is equal to $T_{LOW}$ or $T_{HIGH}$, the next step 256 is implemented.

In step 256 the determination is made as to whether the above measurements are to be performed on another isobar. In the second embodiment, three isobars are measured in which the constant operating pressures vary by approximately 0.5 MPa. The data taken for the two isobars with the lowest and highest constant pressure are used to determine the numerical derivatives as discussed previously. It would be possible to determine these numerical derivatives without taking more than one isobar as is known to those skilled in the art. The measuring of at least three isobars is desirable as it is a relatively accurate method by which to determine the numerical derivatives. In the case of the second embodiment, in step 256, the determination is made as to whether the final isobar has been taken. If it has not, then step 259 is implemented in a new medium 56 (FIG. 5) pressure is determined at which the speed of sound data is measured. After step 259 is performed, step 238 is implemented where the medium 56 (FIG. 5) is brought to either $T_{HIGH}$ or $T_{LOW}$. Note that it would be preferable to alternate the beginning temperatures chosen at step 238 to correlate with the last temperature measured in the previous step 244. In this way the medium will not have to be cooled or heated for the entire range unless data acquisition is performed so as to save on heating and cooling costs. If the final isobar has been taken in step 256, then the data acquisition step 223 (FIG. 6) ends.

Referring now to FIG. 8, shown is a flow chart which illustrates the steps taken during the isochoric convergence of step 229 (FIG. 6) according to the second embodiment. In step 262, the temperature variable is set to equal the lowest temperature value $T_{LOW}$ in the range of temperatures at which the speed of sound u was measured. The temperature variable T is used as a pointer in this context, causing the access to the correlating temperature, speed of sound and pressure data for a specific temperature increment $\Delta T$.

In the next step, the listed progression of calculations previously discussed is executed. When this step is performed for the first time for a particular isobar, the initial values of the compressibility Z and $$\left(\frac{\partial Z}{\partial T}\right)$$

determined in step 226 (FIG. 6) are used in the calculations. Subsequent to the first time step 262 is performed, the compressibility Z and $$\left(\frac{\partial Z}{\partial T}\right)$$

determined in previous calculations are used. The actual calculations performed include the numerical derivative $$\left(\frac{\partial Z}{\partial P}\right)_T,$$

the heat capacity $C_P$, the numerical derivative $$\left(\frac{\partial C_P}{\partial P}\right)_T,$$

the second derivative $$\left(\frac{\partial^2 Z}{\partial T^2}\right)_P,$$

and finally new values for the compressibility Z and the numerical derivative $$\left(\frac{\partial Z}{\partial T}\right).$$

In step 268, the resulting values for Z and $$\left(\frac{\partial Z}{\partial T}\right)$$

are then stored in memory for use in subsequent calculation.

In step 271, an inquiry is made to determine whether the value of the temperature variable T has surpassed the highest temperature $T_{HIGH}$ measured in the specified operating temperature range. If this is not the case then step 274 is executed in which the temperature variable T is incremented by $\Delta T$ and the calculations of step 265 are repeated at the new temperature T. Note that the values for compressibility Z and the numerical derivative $$\left(\frac{\partial Z}{\partial T}\right)$$

resulting from the previous execution of step 265 are used in the current calculations of this step. Each time step 265 is executed, these values will converge to their actual values. In this way an estimate of these parameters is used to start with, and according to the method of the second embodiment, more precise values are obtained. If in step 271, the temperature variable T is greater than $T_{HIGH}$, then execution of step 229 (FIG. 6) ends.

Both the first embodiment relating to the isochoric method and apparatus, and the second embodiment may be employed in conjunction with a pipeline, tank, or any other vessel that will hold a proper medium upon which the forgoing methods may apply. In performing the instant methods, one need only obtain a sample of the medium in a particular vessel. Thus the vessel 53 disclosed herein may be connected to a pipeline, tank or other vessel so as to enable a medium sample to be obtained. Such a connection should also be capable of being closed off so as to allow the isolation of the medium in the vessel 53 for proper measurements to be taken.

Also, the vessel 53 of the first and second embodiments is not restricted to a mere enclosure, but may be a gas pipe or other structure that will allow measurements satisfactory to determine the thermophysical properties in the manner as discussed herein.

In cases where a medium experiences temperature fluctuations of magnitude great enough to encompass several temperature changes equal to an acceptable value for $\Delta T$, one may take measurements of the pressure, temperature, and speed of sound according to the first and second embodiments of the instant invention without temperature control. In such a case the measurements would take place during the temperature fluctuations.

Many variations and modifications may be made to the first and second embodiments of the invention without departing from the spirit and principles of the invention. All such modifications and variations are intended to be included herein within the scope of the present invention, as defined by the following claims.

We claim:

1. A system for determining the thermophysical properties of a multi-component gas, comprising:
   a vessel adapted to retain a gas medium;
   a means for measuring the pressure inside the vessel;
   a means for measuring the temperature inside the vessel;
   a means for measuring the speed of sound inside the vessel;
   a means electrically coupled to said pressure, temperature, and speed of sound measuring means for directing the measurement of the temperature, pressure, and speed of sound of the gas medium at discrete temperature points along an isochore; and
   a means for performing an iterative process employing said temperature, pressure and speed of sound measurements to converge a predetermined initial estimate of a density $\rho$ and a compressibility Z of the gas medium to greater accuracy.

2. The system of claim 1, further comprising a means for altering the density of the gas medium in the vessel.

3. The system of claim 1, further comprising a means for storing the predetermined initial estimates of the density $\rho$, compressibility Z, and the numerical derivative $$\left(\frac{\partial Z}{\partial T}\right)$$

of the gas medium.

4. The system of claim 1, further comprising a means for controlling the temperature of the gas medium in the vessel.

5. The system of claim 1, further comprising a means for agitating the gas medium in the vessel.

6. A system for determining the thermophysical properties of a multi-component gas, comprising:
   a vessel adapted to retain a gas medium;
   a pressure transducer adapted to measure the pressure inside the vessel;
   a temperature probe adapted to measure the temperature inside the vessel;
   a sonic transducer adapted to measure the speed of sound inside the vessel;
   a control system electrically coupled to the pressure transducer, temperature probe, and the sonic transducer adapted to cause the measurement of the temperature, pressure, and speed of sound of the gas medium at discrete temperature points along isochores; and
   a convergence routine within said control system being adapted to perform an iterative process employing said temperature, pressure and speed of sound measurements to converge a predetermined initial estimate of a density p, a compressibility Z, and a numerical derivative $$\left(\frac{\partial Z}{\partial T}\right)$$

of the gas medium to greater accuracy.

7. The system of claim 6, further comprising a solenoid valve connected to the vessel, said valve being adapted to vent an amount of the gas medium from the vessel, thereby altering the density of said gas medium.

8. The system of claim 6, further comprising a memory to store the predetermined initial estimates of the density $\rho$, compressibility Z, and the numerical derivative $$\left(\frac{\partial Z}{\partial T}\right)$$

of the gas medium.

9. The system of claim 6, further comprising a temperature controller adapted to control the temperature of the gas medium in the vessel.

10. The system of claim 6, further comprising an agitator adapted to stir up the gas medium in the vessel.

11. A system for determining the thermophysical properties of a multi-component gas, comprising:
    a vessel adapted to retain a gas medium;
    a pressure transducer adapted to measure the pressure inside the vessel;
    a temperature probe adapted to measure the temperature inside the vessel;
    a sonic transducer adapted to measure the speed of sound inside the vessel;
    a control system electrically coupled to the pressure transducer, temperature probe, and the sonic transducer adapted to direct the measurement of the temperature, pressure, and speed of sound of the gas medium at discrete temperature points along an isochore;
    a memory circuit within said control system for storing the pressure, temperature, and speed of sound measurements and a predetermined initial estimate of a density $\rho$, compressibility Z, and a numerical derivative $$\left(\frac{\partial Z}{\partial T}\right);$$

and
    operating software stored in the memory circuit, said operating software including a code segment adapted to perform an iterative process employing said temperature, pressure and speed of sound measurements to converge the predetermined initial estimates of $\rho$, Z, and $$\left(\frac{\partial Z}{\partial T}\right)$$

of the gas medium to greater accuracy.

12. A method of determining the thermophysical properties of a multi-component gas medium, comprising the steps of:

measuring the temperature, pressure, and speed of sound of said gas medium at discrete temperature points along isochores;

estimating initial values for the compressibility, density, and the partial derivative of the compressibility with respect to temperature of the gas volume;

using said measurements of said temperature, pressure, and speed of sound at said discrete temperature points to converge said initial values of the compressibility, density, and the partial derivative of the compressibility with respect to temperature to greater accuracy via an iterative process; and determining the thermophysical properties of the gas medium based on the compressibility, density and the heat capacity resulting from said convergence step.

13. The method of claim 12, wherein said step of measuring the temperature, pressure, and speed of sound of said gas medium at discrete temperature points further comprises the steps of:

determining an operating temperature range $T_{LOW}$ to $T_{HIGH}$;

adjusting the temperature of said gas medium to equal $T_{LOW}$;

measuring the temperature T, speed of sound u, and pressure P of the gas medium;

storing said measurements of the temperature T, speed of sound u, and pressure P measurements in memory;

raising the temperature T of said medium by an amount equal to said predetermined temperature difference $\Delta T$; and, repeating said steps of measuring and storing T, u, and P, and raising the temperature by $\Delta T$ until the temperature T equals $T_{HIGH}$.

14. The method of claim 13, further including the steps of:
determining whether an additional isochore is to be measured; and,
venting an amount of the gas medium thereby altering the density of the gas medium.

15. The method of claim 12, wherein said step of measuring the temperature, pressure, and speed of sound of said gas medium at discrete temperature points further comprises the steps of:

determining an operating temperature range $T_{LOW}$ to $T_{HIGH}$;

adjusting the temperature of said gas medium to equal $T_{HIGH}$;

measuring the temperature T, speed of sound u, and pressure P of the gas medium;

storing said measurements of the temperature T, speed of sound u, and pressure P measurements in memory;

lowering the temperature T of said medium by an amount equal to said predetermined temperature difference $\Delta T$; and, repeating said steps of measuring and storing T, u, and P, and lowering the temperature by $\Delta T$ until the temperature T equals $T_{LOW}$.

16. The method of claim 15, further including the steps of:
determining whether an additional isochore is to be measured; and,
venting an amount of the gas medium thereby altering the density of the gas medium.

17. The method of claim 12, wherein a single iteration comprises the steps of:

determining the numerical derivative of the initial compressibility Z with respect to density $\rho$ at constant temperature T;

determining the isochoric heat capacity $C_V$;

determining the numerical derivative of the heat capacity $C_V$ with respect to density $\rho$ at constant temperature T;

determining a value for $$\left(\frac{\partial^2 Z}{\partial T^2}\right)_\rho;$$

determining new values for the compressibility Z and $$\left(\frac{\partial Z}{\partial T}\right)$$

using Taylor series approximations; and determining a new value for density $\rho$ based on Z.

18. The method of claim 17, wherein said step of determining the isochoric heat capacity $C_V$ further comprises the step of calculating $C_V$ where $$C_V = \frac{R\left[Z + T\left(\frac{\partial Z}{\partial T}\right)_\rho\right]^2}{u^2\left(\frac{M}{RT}\right) - Z - \rho\left(\frac{\partial Z}{\partial \rho}\right)_T}.$$

19. The method of claim 17, wherein said step of determining a value for $$\left(\frac{\partial^2 Z}{\partial T^2}\right)_\rho$$

further comprises the step of calculating $$\left(\frac{\partial^2 Z}{\partial T^2}\right)_\rho$$

where $$\left(\frac{\partial^2 Z}{\partial T^2}\right)_\rho = -\frac{\frac{\rho}{R}\left(\frac{\partial C_V}{\partial \rho}\right)_T + 2T\left(\frac{\partial Z}{\partial T}\right)_\rho}{T^2}.$$

20. The method of claim 17, wherein said step of determining new values for the compressibility Z and $$\left(\frac{\partial Z}{\partial T}\right)$$

further comprises the step of calculating Z and $$\left(\frac{\partial Z}{\partial T}\right)$$

where $$Z = Z + \Delta T \left(\frac{\partial Z}{\partial T}\right)_\rho + \frac{1}{2}\Delta T^2 \left(\frac{\partial^2 Z}{\partial T^2}\right)_\rho, \text{ and } \left(\frac{\partial Z}{\partial T}\right)_\rho = \left(\frac{\partial Z}{\partial T}\right)_\rho + \Delta T \left(\frac{\partial^2 Z}{\partial T^2}\right)_\rho.$$

21. The method of claim 12, further comprising the step of determining an operating temperature range $T_{LOW}$ to $T_{HIGH}$ within which said temperature, pressure, and speed of sound measurements are taken.

22. The method of claim 21, wherein said step of converging said initial values of the compressibility Z, density $\rho$, and the numerical derivative of the compressibility with respect to temperature $$\left(\frac{\partial Z}{\partial T}\right)$$

further comprises the steps of:
setting a temperature variable T of the gas medium at $T_{LOW}$;
calculating new values for the compressibility Z and the numerical derivative $$\left(\frac{\partial Z}{\partial T}\right);$$

storing the new values for the density $\rho$, compressibility Z and the numerical derivative $$\left(\frac{\partial Z}{\partial T}\right)$$

in memory; and
incrementing the temperature variable T of the gas medium by said predetermined temperature difference $\Delta T$ and repeating said calculating and storing steps until the temperature variable T is equal to $T_{HIGH}$.

23. The method of claim 22, wherein said step of calculating new values for the compressibility Z and the numerical derivative $$\left(\frac{\partial Z}{\partial T}\right)$$

further comprises the calculation of said new values based on said initial values for the density $\rho$, compressibility Z and the numerical derivative $$\left(\frac{\partial Z}{\partial T}\right).$$

24. The method of claim 22, wherein said step of calculating new values for the compressibility Z and the numerical derivative $$\left(\frac{\partial Z}{\partial T}\right)$$

further comprises the calculation of said new values based on the values for density $\rho$, compressibility Z and the numerical derivative $$\left(\frac{\partial Z}{\partial T}\right)$$

calculated before the temperature variable T was incremented by said predetermined temperature difference $\Delta T$.

25. The method of claim 22, further including the steps of:
replacing said initial value for the density $\rho$ with the density $\rho$ determined in said calculating step performed when the temperature variable T is equal to $T_{HIGH}$; and
performing another iteration of said steps of setting, calculating, storing and incrementing steps using the new initial value of the density $\rho$.

* * * * *